United States Patent [19]

Althaus et al.

[11] Patent Number: 5,885,584
[45] Date of Patent: Mar. 23, 1999

[54] REGENERATION OF OLIGODENDROCYTES

[75] Inventors: Hans-Hinrich Althaus, Göttingen; Jürgen Unger, Landshut; Ilse Bartke, Bernried, all of Germany

[73] Assignees: Boehringer Mannheim GmbH, Manheim; Max-Planck-Gesellschaft zur Forderung der Wissenschaften, E.V., Gottingen, both of Germany

[21] Appl. No.: 395,982

[22] Filed: Feb. 28, 1995

Related U.S. Application Data

[63] Continuation-in-part of Ser. No. 30,002, Mar. 19, 1993, abandoned.

[30] Foreign Application Priority Data

Aug. 5, 1991 [DE] Germany .............................. 4125933.5

[51] Int. Cl.$^6$ .............................. A61K 38/16; C07K 14/52
[52] U.S. Cl. ............................ 424/198.1; 514/12; 514/21; 530/350
[58] Field of Search ........................ 514/21, 12; 530/350; 424/198.1

[56] References Cited

U.S. PATENT DOCUMENTS

| 5,082,774 | 1/1992 | Heinrich | 435/69.1 |
| 5,210,185 | 5/1993 | Della Valle et al. | 530/399 |

FOREIGN PATENT DOCUMENTS

| 0 333 574 | 9/1989 | European Pat. Off. . |
| 0333574 | 9/1989 | European Pat. Off. . |

OTHER PUBLICATIONS

Brocke S. et al. 1994. In: "Autoimmune disease models, a guidebook", eds by Cohen, IR. et al. Academic Press, N.Y. pp. 1–14.
Louis, J.C. et al. 1993. Science 259:689–692.
Miller, D.J. et al. 1996. Brain Pathology 6:331–344.
Scolding, N.J. et al. 1995. Neuroscience Letters, 183:75–78.
Cirelli, R. et al. 1995. Clinical Immunotherapeutics, 3:27–87.
Dsouza, S.D. et al. 1996. J. Neuroscience Research, 43:289–298.
Hird, V. et al. 1990. In. Genes and Cancer, Carney D (eds). John Wiley & Son.
Koliatsos et al. 1990 J. Neuro Science, 10:3801–3813.
Mercanti et al. 1977. Biochim. Biophys. Acta 496:412–419.
Poster Abstract: Althaus et al., Proceedings of the 19th Göttingen Neurobiology Conference, "Influence of Growth Factors on Proliferation and Process Regeneration of Cultured Mature Oligondendrocytes", May, 1991. Published in Synapse Transmission Modulation, Proceedings of the 19th Göttingen Neurobiloby Conference (N. Elsmer et al., eds), George Thieme Vertag Stuttgart, New York.
"Porcine Model for Studying the Passage of Non–Depolarizing Neuromuscular Blockers Through the Blood–Brain Barrier", Werba A. et al., *British Journal of Anaesthesia* (1992) 69: 382–386.

"Observations on Remyelination in the Rabbit Spinal Cord Following Domyelination Induced By Lysolecithin", Blakemore, WF, *Neuropath. and Appl. Neurobio.* (1978), 4, 47–59.
"Genetic Factors in Altherosclerosis: Approaches and Model Systems", Monographs in Human Genetics, vol. 12 (1989).
"The Yucatan Miniature Pig and Minimum Stress Methodology in the Laboratory", Panepinto, LM et al., 8th ICLAS/CALS Symp., Vancouver 1983.
"Development of a Piglet Model of Status Epilepticus: Preliminary Results", Terndrup, TE et al., *Laboratory Investigation*, Feb. 1993.
"Epithelial Wound Healing Enhanced by Transforming Growth Factor–$\alpha$ and Vaccinia Growth Factor", Schultz, TS et al., *Science*, vol. 235, pp. 350–352.
"Nerve–growth factor induced proliferation and enhances fiber regeneration in oligodendrocytes isolated from adult pig brain", *Neurosci. Letters*, 135, (1992) pp. 219–223.
"Interferon beta–1b is effective in relapsing–remitting multiple sclerosis" Paty, DW et al., *Neurology*, Apr. 1993, pp. 662–667.
"Growth regulation of skin cells by epidermal cell–derived factors: application for wound healing", Eisinger, et al., *Natl. Acad. Sci.*, USA, pp. 1937–1941, Mar. 1988.
"Isolation of Human Nerve Growth Factor From Placental Tissue", Goldstein et al., *Neurochemical Research* (3), pp. 175–183, 1978.
Halbrook et al., "Production and Characterization of Biologically Active Recombinant Beta Nerve Growth Factor", *Mol. & Cell. Biology*, Jan. 1988, pp. 452–456.
Calbiochem–Catalogue (1990–1991), p. 21, Catalogue #616398.
Schröter et al., "The Phorbolester TPA Dramatically Accelerates Oligodendroglial Process Regeneration", Naturwissenschaften 74, pp. 393–394 (1987).
Hama et al., "Protein kinase C as a component of a nerve growth factor–sensitive phosphorylation system in PC12 cells", *Proc. Natl. Acad. Sci.*, vol., 83, pp. 2353–2357, Apr. 1986.

(List continued on next page.)

*Primary Examiner*—Lila Feisee
*Assistant Examiner*—Geetha P. Bansal
*Attorney, Agent, or Firm*—Nikaido Marmelstein Murray & Oram, LLP

[57] ABSTRACT

The invention concerns a process for improving the regeneration of oligodendrocytes, in particular of human oligodendrocytes, in which oligodendrocytes are treated in cell culture with nerve growth factor (NGF) or active fragments of NGF. Furthermore a composition is disclosed for treating diseases in which a demyelination of nerve fibres occurs which contains NGF or an active fragment thereof as the active substance, if desired, together with the usual pharmaceutical vehicles, auxiliary substances, fillers and diluents.

9 Claims, 8 Drawing Sheets

OTHER PUBLICATIONS

Althaus et al., "Nerve growth factor induces proliferation and enhances fiber regeneration in oligodendrocytes isolated from adult pig brain", *Neuroscience Letters*, 135 (1992), pp. 219–223.

Althaus, et al., "Protein Kinase C Stimulation Enhances the Process Formation of Adult Oligodendrocytes and Induces Proliferation", *Journal of Neuroscience Research*, vol. 29, pp. 481–489, Aug. 1991.

Hall et al., "Suppression of Nerve Growth Factor–directed Neurite Outgrowth in PC12 Cells by Sphingosine, and Inhibitor of Protein Kinase C*", *The Journal of Biological Chemistry*, vol. 263, No. 9, May 1987, pp. 4460–4466.

Althaus et al., "Protein Kinases A And C Are Involved In Oligodendroglia Process Formation", Nato Asi Series, vol. H 43, *Cellular and Molecular Biology of Myelination*, pp. 248–253, 1989.

Hunter et al., O–2A Glial Progenitors From Mature Brain Respond to CNS Neural Cell Line–Derived Growth Factors, *Journal of Neuroscience Research*, vol. 28, pp. 574–582, 1991.

Althaus et al., "Isolation and Cultivation of Mature Oligodendroglial Cells", Naturwissenschaften 71, pp. 309–315, 1984.

Lillien et al., "Nerve growth factor is a mitogen for cultured chromaffin cells", *Letters to Nature*, vol. 317, Oct. 1985, pp. 632–634.

Gebicke–Härter et al., "Bulk Separation and Long–Term Culture of Oligodendrocytes from Adult Pig Brain. I Morphological Studies", *Journal of Neurochemistry*, New York, 1984, pp. 257–368.

REGENERATION OF OLIGODENDROCYTES

The present application is a continuation in part of application Ser. No. 08/030,002, filed on Mar. 19, 1993, abandoned.

DESCRIPTION

The present invention concerns a process for improving the regeneration of oligodendrocytes, in particular of human oligodendrocytes. In addition the invention concerns a pharmaceutical composition for treating diseases in which a demyelination of nerve fibres occurs as well as a process for its production.

The covering of nerve fibres in the central nervous system (CNS) with myelin is essential for the function of neuronal signal transmission. The myelin sheath is formed by oligodendrocytes (OL) the fibres of which wrap around the axon of a nerve cell. Diseases such as multiple sclerosis in which the myelin sheath of the axon is damaged or destroyed also lead to damages of the OL. In contrast to the peripheral nervous system (PNS), a remyelination of nerve cells in the adult CNS is functionally inactive. Therefore the identification and characterization of factors which are responsible for the regeneration of OL is very important for the molecular understanding of demyelinating diseases and for the development of therapeutic agents.

Mature oligodendrocytes isolated from adult porcine brain regenerate when cultured in vitro and form a fibre network within 14 days (Althaus et al. (1984), "Naturwissenschaften" 71, 309–315). These OL cultures are therefore an excellent test system for identifying substances which stimulate the regeneration of OL. Using this system it has already been shown that phorbol esters such as phorbol-12-myristate-13-acetate (TPA) can considerably increase the fibre regeneration of the OL.

Phorbol esters occur in the milky exudate of snakeweed plants or in croton oil from the seeds of the indian Croton tiglium. However, they are completely unsuitable as potential drugs for the treatment of demyelinating diseases since they act as local irritants and are cocarcinogenic.

The object of the present invention was therefore to find a substance which acts to improve the regeneration of oligodendrocytes and at the same time is not toxic.

The object according to the present invention is achieved by a process for improving the regeneration of oligodendrocytes, in particular of human oligodendrocytes, which is characterized in that oligodendrocytes are treated in cell culture with nerve growth factor (NGF) or active fragments of NGF.

The term "NGF" or "active fragment of NGF" within the sense of the present invention refers to natural NGF, in particular to natural human or murine NGF and all fragments or derivatives of NGF which have its biological activity i.e. cause an improvement of the fibre regeneration of oligodendrocytes in vitro or/and the proliferation of mature oligodendrocytes. Examples of NGF molecules which are suitable for the process according to the present invention are for instance NGF-β, NGF 2.5S or NGF 7S from the submaxillary gland of the mouse. These NGF molecules can for example be obtained commercially from Sigma-St.Louis or Boehringer Mannheim. The process according to the present invention is preferably carried out with a human NGF, particularly preferably with human recombinant NGF-β. The production of an active NGF fragment by tryptic digestion of NGF is described by Mercanti et al. (Biochim. Biophys. Acta 496 (1977), 412–419). This fragment is composed of two linear oligopeptides which are linked by a disulfide bridge and contains the amino acid residues 10 to 25 and 75 to 88 of the amino acid sequence of NGF (according to the nomenclature of Angeletti and Bradshaw (1970), Proc. Natl. Acad. Sci. USA 68, 2417–2421).

When oligodendrocytes are treated in cell culture with NGF (NGF 2.5S or human recombinant NGF) the fibre regeneration of the OL was improved in a similar manner to treatment with phorbol esters but with a slightly different time course. Thus when OL were treated with phorbol esters a fibre network was already formed after 24 hours, while 48 hours were necessary for this in the presence of NGF. The NGF action was inhibited by anti-NGF antibodies.

Increasing active concentrations of NGF did not result in a more rapid regeneration of the OL fibres it was, however, found that the extent of fibre elongation and branching was dependent on the concentration. The fibre production in all oligodendrocytes which survived at least the examination period (2 weeks) could be improved by NGF.

In addition it was found that NGF 2.5S induces the proliferation of a subclass of cultured mature OL. Similar results were obtained with human recombinant NGF. This effect was dependent on concentration and did not occur until the cells had been treated for more than 24 hours with NGF. The induction of proliferation was blocked by anti-NGF antibodies. The highest rate of NGF proliferation was found when the cells were treated with a combination of phorbol ester and NGF.

The action of NGF can also be improved when the oligodendrocytes are treated with a combination of NGF and one or several protease inhibitors. An example of a suitable and preferred protease inhibitor is aprotinin which is for example sold by Bayer-Leverkusen under the trade name "Trasylol".

The present invention also concerns a pharmaceutical composition for the treatment of diseases in which a demyelination of nerve fibres occurs and which contains NGF or an active fragment thereof as the active substance, if desired, together with the usual pharmaceutical vehicles, auxiliary substances, fillers and diluents. The pharmaceutical composition preferably contains human NGF, especially human recombinant NGF-β. In addition the composition can contain one or several pharmaceutically tolerated protease inhibitors, for example aprotinin.

Furthermore the invention concerns a process for the production of a pharmaceutical composition for the treatment of diseases in which a demyelination of nerve fibres occurs which contains NGF or an active fragment thereof as the active substance, if desired, together with the usual pharmaceutical vehicles, auxiliary substances, fillers and diluents in which one preferably uses human NGF, particularly preferably human recombinant NGF-β, as the active substance.

In order to produce pharmaceutical preparations, the composition according to the present invention can be processed with therapeutically acceptable vehicles. Suitable vehicles for the production of such solutions are water, polyols, sucrose, invert sugar and glucose. Suitable vehicles for injection solutions are water, alcohols, polyols, glycerol and vegetable oil.

In addition the pharmaceutical preparations can contain preservatives, solvents, stabilizing agents, wetting agents, emulsifiers, salts for changing the osmotic pressure, buffers and, if desired, other therapeutic drugs.

Diseases in which a demyelination of nerve fibres occurs and which can be treated with the aid of the pharmaceutical composition according to the present invention can for example be caused by inflammations, autoimmune processes, enzymes or toxins. Examples of such diseases are for instance multiple sclerosis, slow virus encephalitis, various forms of myelitis or heavy metal poisoning.

The composition according to the present invention is preferably administered systemically. The administration can be carried out by methods familiar to a person skilled in the art, for example intracisternally, intravenously or peripherally. For the intracisternal or intravenous administration, NGF can be suspended for example in physiological saline.

The addition of protease inhibitors, e.g. aprotinin, is not absolutely necessary when NGF is administered daily but does afford protection against proteases which could inactivate NGF. The preferred lower limit for the daily administered NGF dose is at a concentration of 10 ng NGF/ml blood, whereas the preferred upper limit is 300 ng NGF/ml. The administration of NGF is preferably carried out over a longer time period, i.e. at least 48 hours.

It is intended to elucidate the present invention further by the following examples in conjunction with FIGS. 1 and 2.

EXAMPLE 1

Culturing of Oligodendrocytes

Oligodendrocytes were isolated from corpus callosum of about one-year old pigs by a density gradient and subsequently cultured (Gebicke-Härter et al. (1984), J. Neurochem. 42, 357–368). The cells were sown on Petri dishes coated with poly-D-lysine and cultured in a medium consisting of MEM/HAM's F-10 (1:1 v/v), 10% foetal calf serum, transferrin (10 µg/ml), insulin 5 µg/ml and mezlocillin (40 µg/ml) under the usual culture conditions (5% $CO_2$, 37° C.). Based on their surface characteristics the cells were mature oligodendrocytes, they were immunocytochemically GC$^+$, WP$^+$(marker for mature OL), $A_2B_5^-$ (marker for OL precursor cells) and OX42$^-$ (marker for microglia cells). Monoclonal antibodies and polyclonal antisera were used as the markers.

EXAMPLE 2

Growth of Oligodendrocyte Fibres in the Presence of NGF

Figure 1:
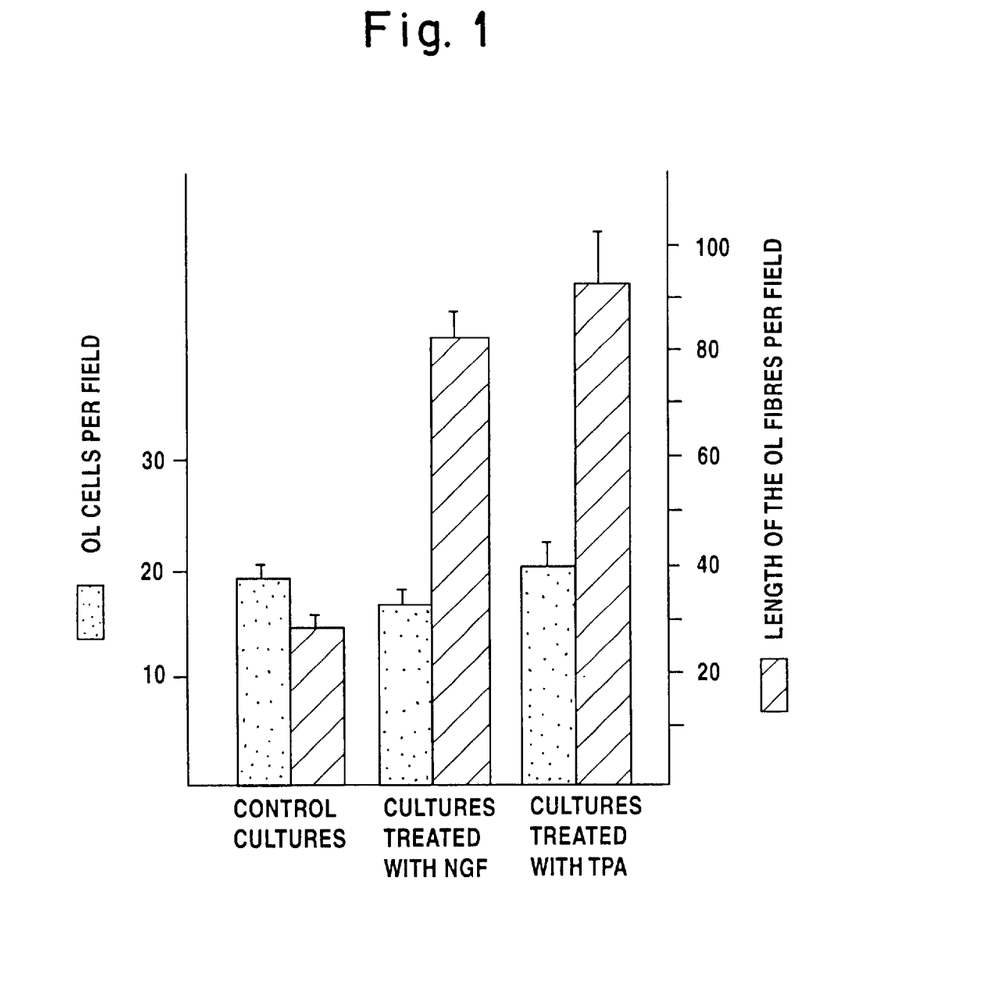
FIG. 1 shows the fibre growth of oligodendrocytes in the presence of NGF.

After 6 days culture of the oligodendrocytes from example 1 in vitro NGF (human recombinant NGF-β, 100 ng/ml) and Trasylol (1000 U/ml, Bayer Leverkusen) were added to the culture medium which was renewed daily. The protease inhibition caused by Trasylol resulted in a more constant NGF level during the culture. After treatment for two days the cells were fixed and examined by electron microscopy. FIG. 1 shows a comparison of the fibre length between untreated control cells, cells treated with NGF and cells treated with phorbol ester (TPA). The fibre length which was determined by means of enlarged phase-contrast photographs, showed a statistically significant difference (t-test, fibre length/number of cells, $p<0.001$) in control cultures and cultures treated with NGF, as was also the case in cultures treated with TPA.

EXAMPLE 3

Proliferation of Mature Oligodendrocytes in the Presence of NGF

Oligodendrocytes coated with poly-D-lysine on multiwell culture plates (160 000 cells/well) were treated in vitro after 6 days with various growth factors (plus Trasylol) at the concentrations shown in table 1 whereby the culture medium was renewed daily. The proliferation of oligodendrocytes was measured at 24-hour intervals by means of [$^3$H] thymidine incorporation. Each treatment was carried out twice and repeated at least twice. The standard deviations between individual samples was in the range 20 to 25%.

TABLE 1

| Tested substance | OL fibre formation | Origin of the substance |
|---|---|---|
| 1. NGF (2.5 S) (10–300 ng/ml) | + | submaxillary gland of the mouse |
| 2. NGF (2.5 S) (100 ng/ml) + anti-NGF/1:200) | = | rabbit (polyclonal) |
| 3. NGF-β (10–100 ng/ml) | + | human, recombinant |
| 4. Trasylol (1000 U/ml) | = | trade name of aprotinin, Bayer Leverkusen |
| 5. Interleukin-2 (100–1000 U/ml) | = | human, recombinant |
| 6. EGF (1–100 ng/ml) (epidermal growth factor) | = | submaxillary gland of the mouse |
| 7. FGF (a/b) (1–200 ng/ml) (fibroblast growth factor) | = | bovine |
| 8. IGF I/II (10–100 ng/ml) (insulin-like growth factor) | = | human, recombinant |
| 9. PDGF (2–10 ng/ml) (platelet derived growth factor) | = | human platelet cells |

The various growth factors were obtained from Sigma-St. Louis (1,2,5,7,9) and Boehringer Mannheim (1–3, 8). 10% foetal calf serum was added to the culture medium which was renewed daily and contained the growth factors at the final concentrations stated above +1000 U/ml Trasylol. In IGF I and II the usual insulin concentration was reduced from 5 µg to 0.5 µg/ml. The fibre formation was classified as follows:

= some short fibres (with a length of 3–4 times the body diameter) and very few branches present, corresponding to the control cultures;

+ fibre network with increased metabolism.

Figure 2:
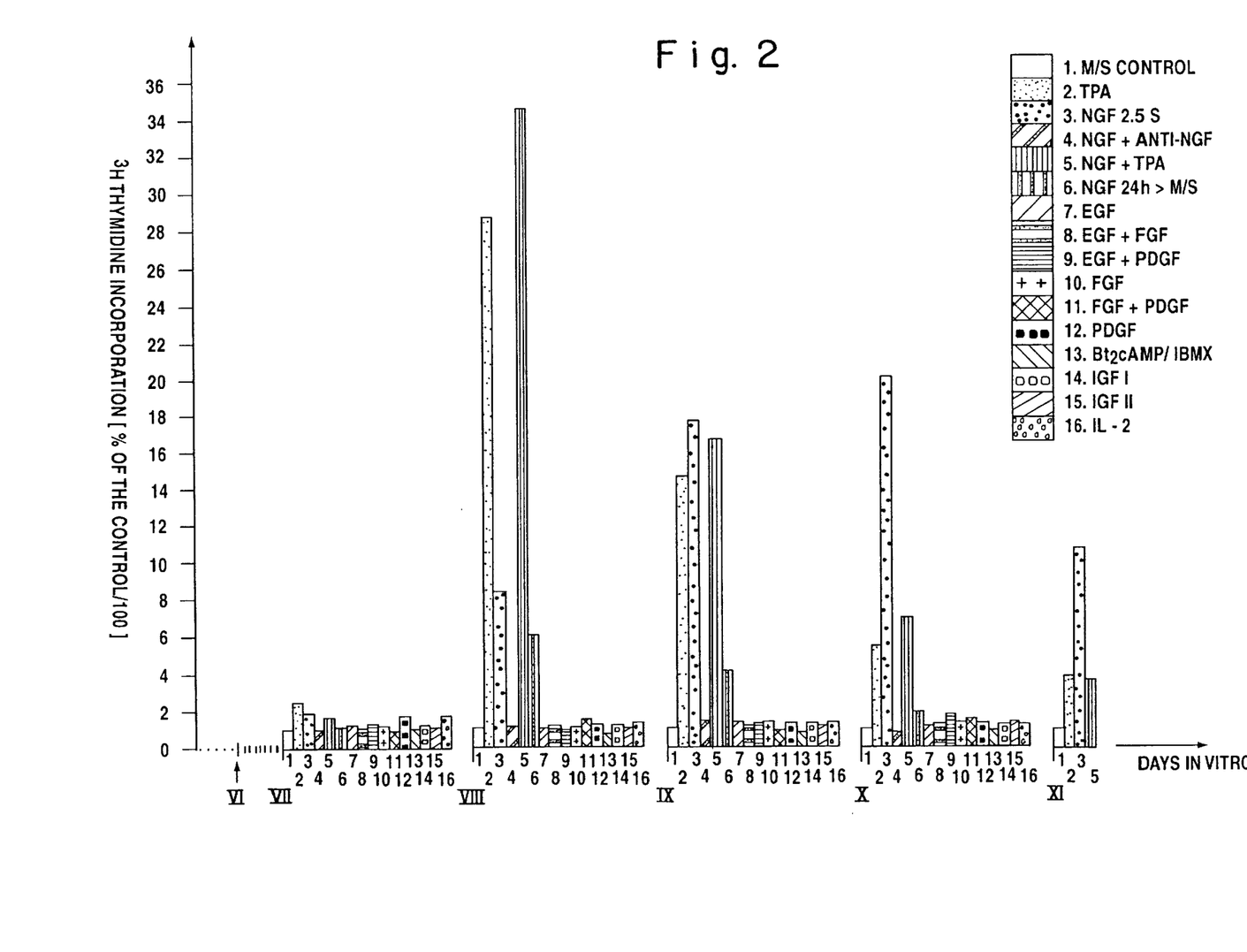
FIG. 2 shows the incorporation of ($^3$H) thymidine into cultured oligodendrocytes in the presence of various growth factors.

FIG. 2 shows the incorporation of [$^3$H] thymidine in the presence of various growth factors. From this it is apparent that apart from phorbol ester (TPA) only NGF shows an effect on the proliferation of OL. In the presence of anti-NGF antibodies the cell proliferation induced by NGF is completely inhibited.

EXAMPLE 4

Demyelination:

An experimental model for demyelination was established in the female, adult "Göttingen Mini Pig" (age: 10–14 months, weight: 25–30 kg) by stereotaxic injection of lysolecithin (LL, 5 µl of 1% LL in 0.9% saline over a period of 15 min.) into the subcortical white matter of the brain. It is known from previous studies that this infusion causes a rapid reduction of myelin sheaths within the diffusion area of the detergent (Blakemore, 1978). No data have been available on pig brains so far.

NGF—application:

Immediately after LL-application, a stainless steel needle was implanted in the center of the lesion area and affixed with IONOCEM, a ionomeric bonding bone cement (IONOS Seefeld, Germany). An ALZET osmotic pump (200 $\mu$l volume, infusion rate: 0.5 $\mu$l/h) was connected with the needle and implanted subcutaneously.

Way of application: Directly intracerebral, beyond the blood-brain-barrier

Application interval: 7–20 days

Concentration of NGF: 1 mg/ml, dissolved in PBS, pH 7.2–7.4

Dosages: 0.5 $\mu$g/h=3–10 $\mu$g/kg/interval

Controls:

Replacement of NGF-solution with PBS or an equal dose (1 mg/ml) of Cytochrome C.

Evaluation of NGF—effects:

At the end of the NGF-(control,respectively) application period, the experimental animals were sacrificed, the brain was removed and prepared for histological examination: The areas of interest were studied with routine histological (H.E. staining, Luxol Fast Blue staining) and immunocytochemical (myelin basic protein—MBP) procedures.

Figure 3A:
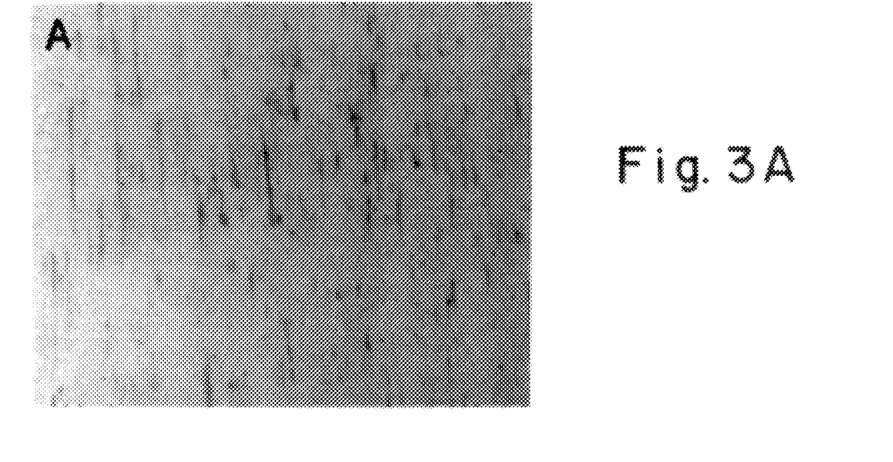
-- FIGS. 3A and 3B are photomicrographs of representative histological sections depicting an area of demyelination (A) c mpared to a control (B).
Figure 3B:
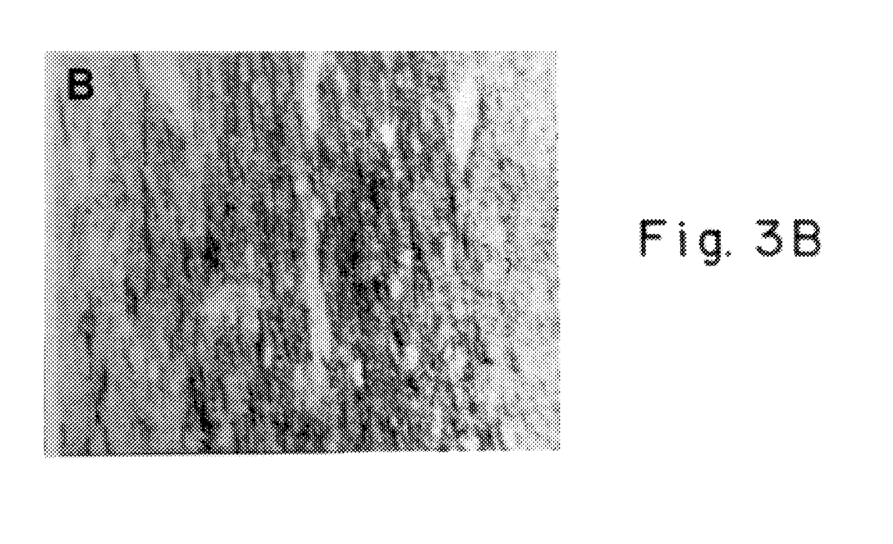
Figure 3C:
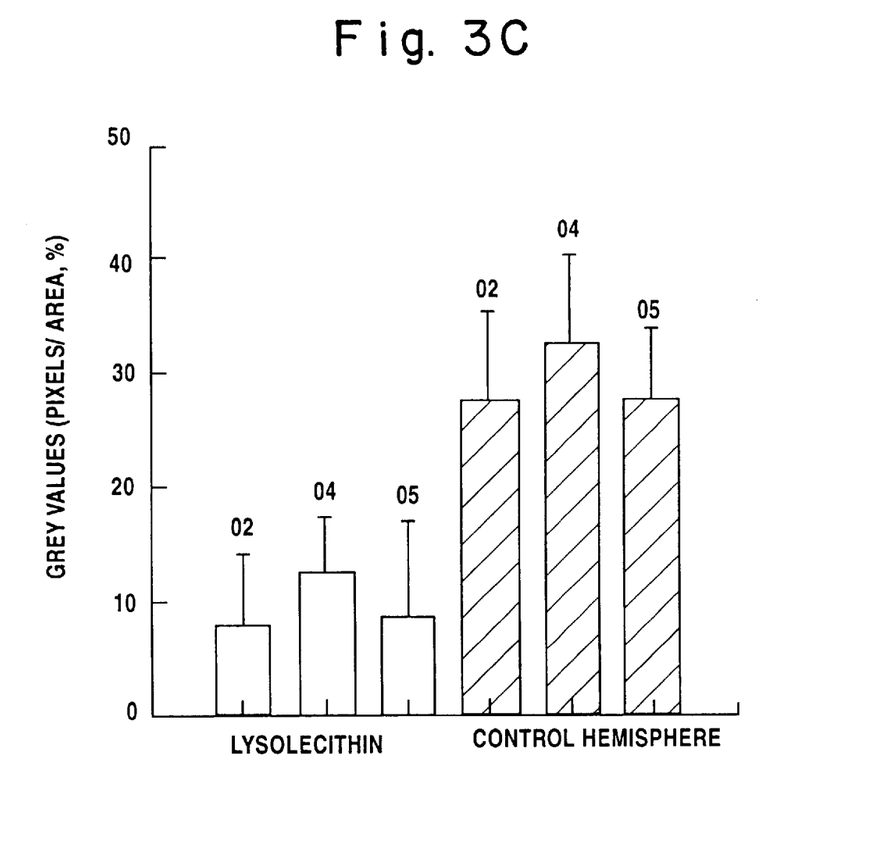
FIG. 3C is a densitometric analysis of myelin basic protein-immunoreactive fibers: controls versus lysolecithin-lesions (1 week post lesioning) The values represent mean +/- SD from measurements of 18 areas per animal (number = individual animal)
Figure 4A:
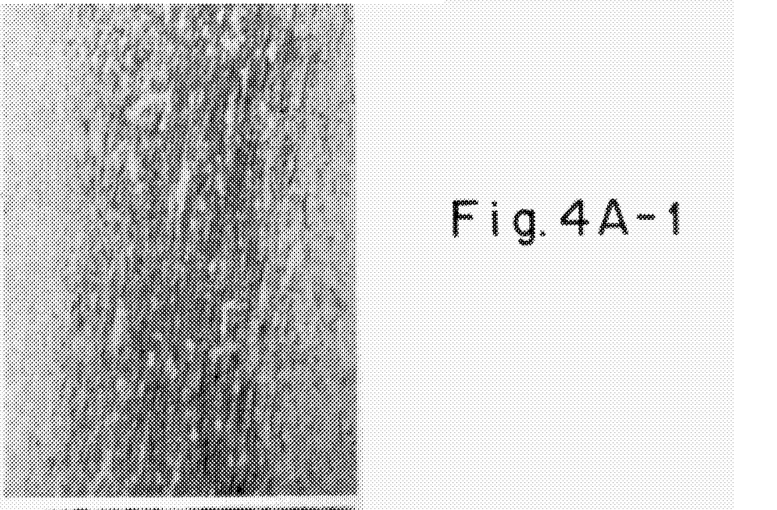
Figure 4A:
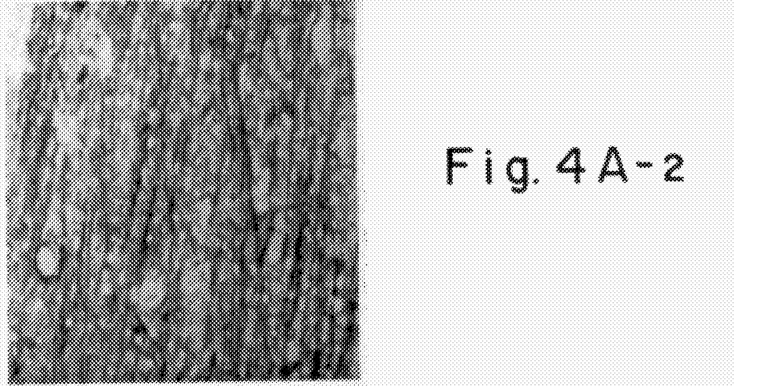
Figure 4A:
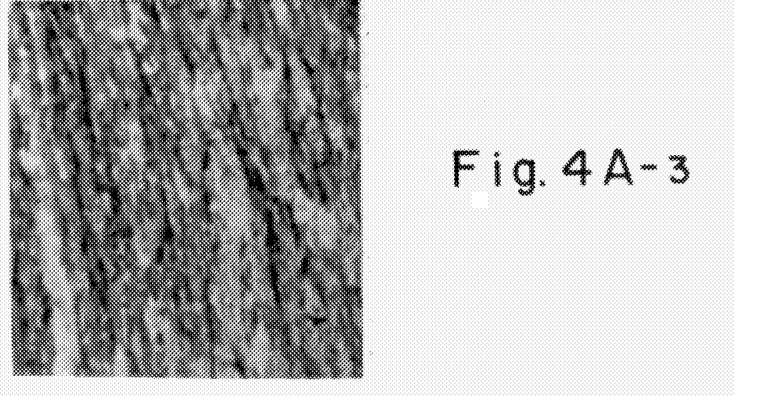
Figure 4B:
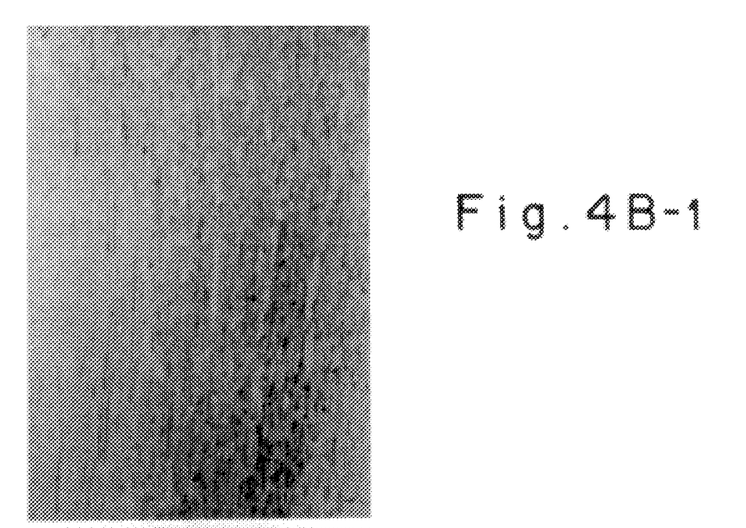
Figure 4B:
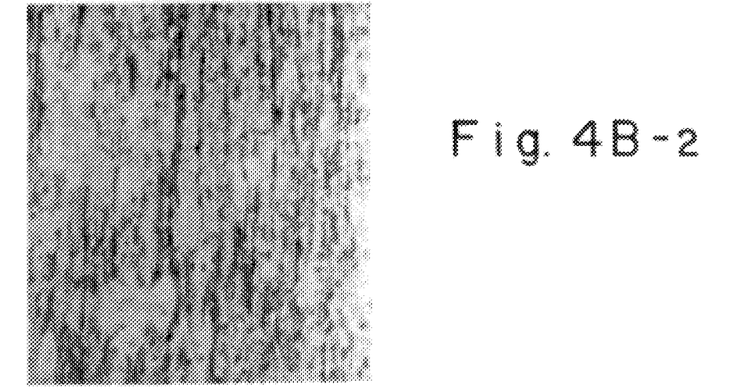
Figure 4B:
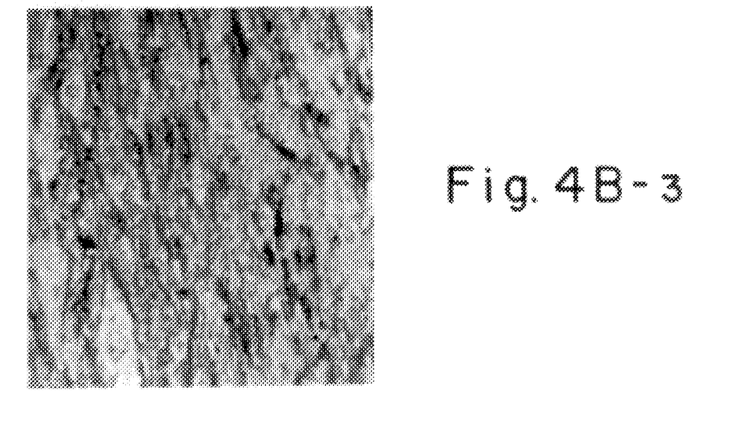

Findings:

Injection of LL causes a widespread demyelination throughout the area of diffusion (FIG. 3).

Figure 5A:
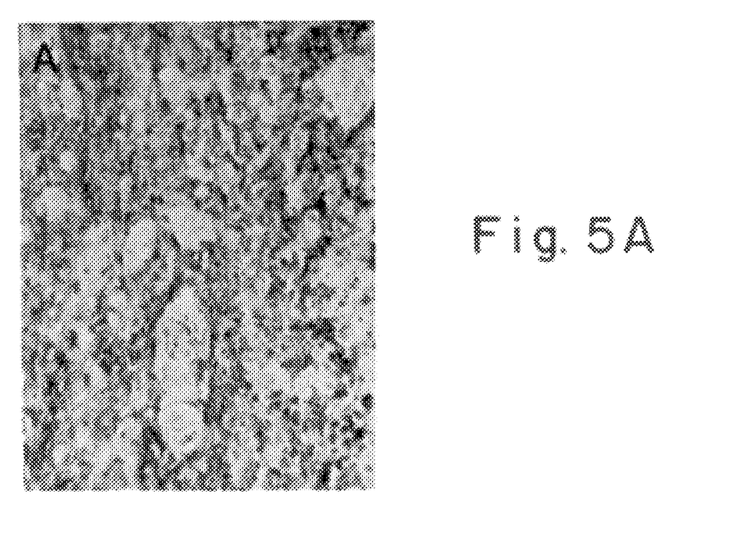
FIGS. 5A and 5B are photomicrographs of representative histological sections depicting MBP-immunoreactive fibers in an animal receiving NGF (A) versus sham treatment (B). Significant remyelination is seen after 12 days of NGF-infusion.
Figure 5B:
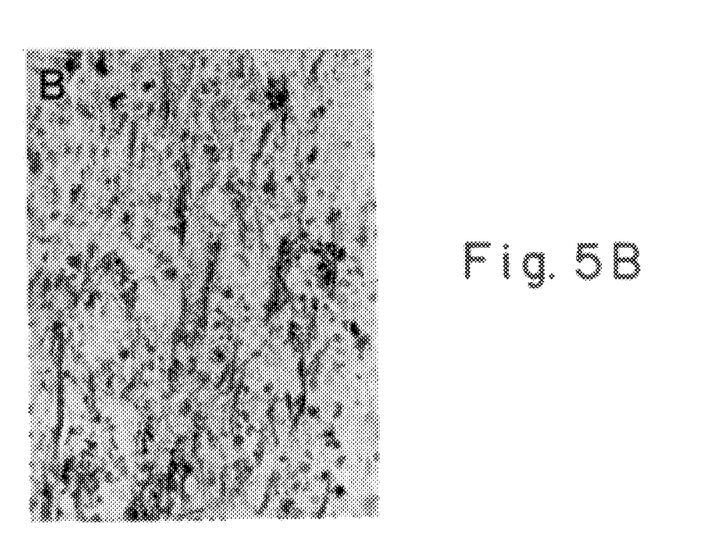
Figure 5C:
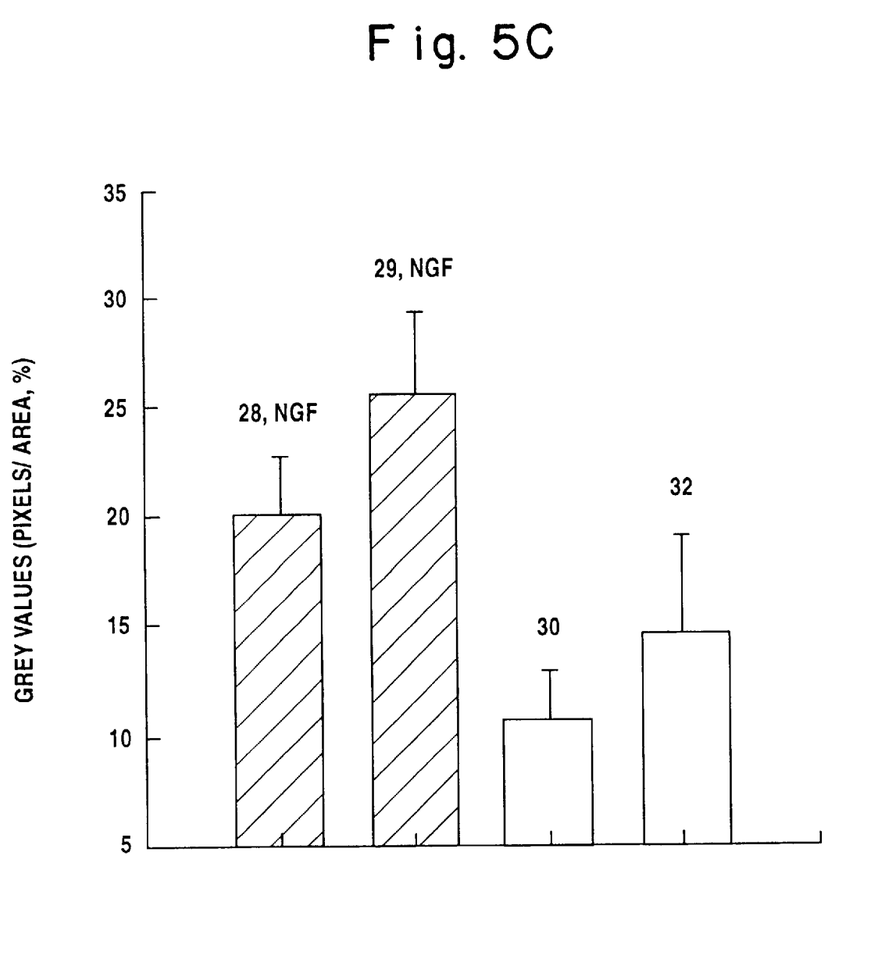
FIG. 5C is a densitometric analysis of MBP-immunoreactive fibers in lesioned animals treated with NGF for 12 days (no. 28, 29) and in sham-treated animals (no. 30-32). The values represent mean +/- SD from measurements of 18 areas per animal.--

Under infusion of NGF an improved and accelerated remyelination of the lesioned nerve fibers was detected within the application interval as compared to controls (FIGS. 4 and 5). Significant regeneration was observed as early as 7–12 days after lesioning. These findings were confirmed by densitometric analysis of myelin basic protein-immunoreactivity in histological sections (FIGS. 3 and 5).

The data strongly support the earlier in vitro data that NGF is a highly effective protein for the proliferation of mammalian oligodendrocytes and thus a potential therapeutic substance for demyelinating diseases, i.e. multiple sclerosis.

Additional supporting data:

There is a clear correlation between the degree of remyelination and functional improvements in the state of demyelinating diseases (IFN$\beta$ study group, 1993).

Data obtained from animal models using pigs have a great clinical relevance in biomedical research, i.e. numerous studies on the cardiovascular system, skin and peripheral nervous system that have proven that data from procine tissue are applicable on human subjects).

REFERENCES

Althaus H. H., Klöppner S., Schmidt-Schultz T., Schwartz P. (1992) Nerve growth factor induces proliferation and enhances fiber regeneration in oligodendrocytes isolated from adult pig brain. Neurosci. Lett 135:219–123

Blakemore W. F. (1978) Observation on remyelination in the rabbit spinal cord following demyelination induced by lysolecithin. Neuropathol. Appl. Neurobiol. 4:47–59.

The IFN$\beta$ multiple sclerosis study group. (1993) Interferon beta-1b is effective in relapsing remitting multiple sclerosis. I. Clinical results of a multicenter, randomized, double-blind, placebo-controlled trial. Neurology 43:662–667.

We claim:

1. A process to improve the growth and proliferation of oligodendrocytes or to improve and accelerate the remyelination of lesioned nerve fibers for diseases in which a demyelination of nerve fibers occurs, comprising administering a composition which contains an amount of NGF, NGF 2.5S or NGF 7S.

2. The process according to claim 1, wherein the composition is administered intravenously.

3. A process for improving the growth and proliferation of oligodendrocytes comprising administering human or mouse nerve growth factor (NGF), NGF 2.5S or NGF 7S to a mammal in need of such treatment.

4. A process for improving and accelerating remyelination of lesioned nerve fibers, comprising administering human or mouse nerve growth factor (NGF), NGF 2.5S or NGF 7S to a mammal in need of such treatment.

5. The process according to claim 4, wherein said mammal is suffering from a demyelinating disease.

6. The process according to claim 4, wherein said mammal is a human.

7. The process according to claim 5, wherein said demyelinating disease is multiple sclerosis.

8. The process according to claim 4, wherein said nerve growth factor is administered at between 3–10 $\mu$g/kg/interval.

9. The process according to claim 4, wherein said nerve growth factor is administered at a treatment interval of between 7–20 days.

\* \* \* \* \*

UNITED STATES PATENT AND TRADEMARK OFFICE
CERTIFICATE OF CORRECTION

PATENT NO. : 5,885,584
DATED : March 23, 1999
INVENTOR(S) : Hans-Hinrich Althaus, et al.

It is certified that error appears in the above-identified patent and that said Letters Patent is hereby corrected as shown below:

Column 3, line 21, change "FIGS. 1 and 2" to --FIGS. 1-5--.

Column 3, between lines 21 and 22, insert the heading --Brief Description of the Drawings--.

Column 3, line 23, after "and" insert --TPA--.

Column 3, between lines 26 and 27, insert

FIGS. 4A-1, 4A-2, 4A-3, 4B-1, 4B-2, and 4B-3 are low and high power magnifications of immunocytochemical staining of myelin basic protein (MBP) in the subcortical white matter of lysolecithin-lesioned animals after NGF-infusion (4A-1, 4A-2, and 4A-3) or sham-treatment (4B-1, 4B-2, and 4B-3) over a period of 12 days. Under chronic intracerebral NGF-infusion a significant increase in staining intensity and number of myelinated fibers is observed. The findings are representative for all groups and animals studied.

UNITED STATES PATENT AND TRADEMARK OFFICE
CERTIFICATE OF CORRECTION

PATENT NO. : 5,885,584
DATED : March 23, 1999
INVENTOR(S) : Hans-Hinrich Althaus, et al.

It is certified that error appears in the above-identified patent and that said Letters Patent is hereby corrected as shown below:

Signed and Sealed this

Third Day of August, 1999

Q. TODD DICKINSON

*Attest:*

*Attesting Officer*          Acting Commissioner of Patents and Trademarks